US007098041B2

(12) United States Patent
Kaylor et al.

(10) Patent No.: US 7,098,041 B2
(45) Date of Patent: Aug. 29, 2006

(54) METHODS TO VIEW AND ANALYZE THE RESULTS FROM DIFFRACTION-BASED DIAGNOSTICS

(75) Inventors: Rosann Marie Kaylor, Cumming, GA (US); Difei Yang, Alpharetta, GA (US); Zdravko Savov Atanassov, Alpharetta, GA (US); Michael Eugene Knotts, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 699 days.

(21) Appl. No.: 10/013,972

(22) Filed: Dec. 11, 2001

(65) Prior Publication Data

US 2006/0160245 A1 Jul. 20, 2006

(51) Int. Cl.
*G01N 33/543* (2006.01)

(52) U.S. Cl. .................. 436/518; 385/12; 385/129; 385/130; 385/131; 356/317; 356/318; 356/347; 422/55; 422/57; 422/82.08; 422/82.11; 435/7.21; 435/7.9; 435/7.92; 435/7.94; 435/287.1; 435/287.2; 435/288.7; 435/808; 436/164; 436/172; 436/524; 436/525; 436/527; 436/805

(58) Field of Classification Search ............... 385/12, 385/129, 130, 131; 356/317, 318, 347; 422/55, 57, 82.08, 82.11; 435/7.21, 7.9, 435/7.92, 7.94, 287.1, 287.2, 288.7, 808; 436/164, 172, 518, 524, 525, 527, 805
See application file for complete search history.

(56) References Cited

U.S. PATENT DOCUMENTS

| | | | |
|---|---|---|---|
| 3,641,354 A | 2/1972 | De Ment | |
| 3,716,359 A | 2/1973 | Sheridon | |
| 3,884,553 A * | 5/1975 | Graser, Jr. ................. | 359/562 |
| 4,011,009 A | 3/1977 | Lama et al. | |
| 4,094,647 A | 6/1978 | Deutsch et al. | |
| 4,274,706 A | 6/1981 | Tangonan | |
| 4,312,228 A | 1/1982 | Wohltjen | |
| 4,363,874 A | 12/1982 | Greenquist | |
| 4,399,686 A | 8/1983 | Kindlund et al. | |
| 4,416,505 A | 11/1983 | Dickson | |
| 4,426,451 A | 1/1984 | Columbus | |
| 4,477,158 A | 10/1984 | Pollock et al. | |
| 4,528,260 A | 7/1985 | Kane | |
| 4,534,356 A | 8/1985 | Papadakis | |
| 4,552,458 A | 11/1985 | Lowne | |
| 4,561,286 A | 12/1985 | Sekler et al. | |
| 4,562,157 A | 12/1985 | Lowe et al. | |
| 4,596,697 A | 6/1986 | Ballato | |
| 4,608,344 A | 8/1986 | Carter et al. | |
| 4,632,559 A | 12/1986 | Brunsting | |
| 4,636,626 A * | 1/1987 | Hazama et al. ......... | 250/201.4 |
| 4,661,235 A | 4/1987 | Krull et al. | |
| 4,690,715 A | 9/1987 | Allara et al. | |
| 4,727,019 A | 2/1988 | Valkirs et al. | |
| 4,776,944 A | 10/1988 | Janata et al. | |
| 4,802,951 A | 2/1989 | Clark et al. | |
| 4,812,221 A | 3/1989 | Madou et al. | |
| 4,815,843 A | 3/1989 | Tiefenthaler et al. | |
| 4,818,710 A | 4/1989 | Sutherland et al. | |
| 4,837,715 A | 6/1989 | Ungpiyakul et al. | |
| 4,842,633 A | 6/1989 | Kuribayashi et al. | |
| 4,842,783 A | 6/1989 | Blaylock | |
| 4,844,613 A | 7/1989 | Batchelder et al. | |
| 4,851,816 A | 7/1989 | Macias et al. | |
| 4,857,453 A | 8/1989 | Ullman et al. | |
| RE33,064 E | 9/1989 | Careter et al. | |
| 4,871,258 A | 10/1989 | Herpichboehm et al. | |
| 4,876,208 A * | 10/1989 | Gustafson et al. .......... | 436/531 |
| 4,877,586 A | 10/1989 | Devaney, Jr. et al. | |
| 4,877,747 A | 10/1989 | Stewart | |
| 4,882,288 A | 11/1989 | North et al. | |
| 4,895,017 A | 1/1990 | Pyke et al. | |
| 4,916,056 A | 4/1990 | Brown, III, Et al. | |
| 4,931,384 A | 6/1990 | Layton et al. | |
| 4,963,498 A | 10/1990 | Hillman et al. | |
| 4,992,385 A | 2/1991 | Godfrey et al. | |
| 4,999,489 A | 3/1991 | Huggins | |
| RE33,581 E | 4/1991 | Nicoli et al. | |
| 5,023,053 A | 6/1991 | Finlan | |
| 5,026,653 A | 6/1991 | Lee et al. | |
| 5,035,863 A | 7/1991 | Finlan et al. | |

(Continued)

FOREIGN PATENT DOCUMENTS

DE 20000122 4/2000

(Continued)

OTHER PUBLICATIONS

Abstract of Japanese Patent No. JP2085755.

(Continued)

*Primary Examiner*—Christopher L. Chin
(74) *Attorney, Agent, or Firm*—Dority & Manning, P.A.

(57) ABSTRACT

An analyzer useful in determining the presence of an analyte using a diffraction based sensing device and methods and systems using this device. The present invention may be used with a variety of different diffraction-based diagnostic methods and systems. The analyzer enhances the accuracy and/or usefulness of these devices in detecting analytes, while providing more ease-of-use and convenience to the user. The analyzer may include a light source, a photodiode, a microprocessor and a display system for informing the user of the result. Other features include mirrors, lenses, a sample holder, and a mask for blocking out some light. The analyzer and related method and system may be used in a large number of environments, including commercial, professional, and individual.

23 Claims, 6 Drawing Sheets

U.S. PATENT DOCUMENTS

| | | | |
|---|---|---|---|
| 5,055,265 A | 10/1991 | Finlan | |
| 5,057,560 A | 10/1991 | Mueller | |
| 5,063,081 A | 11/1991 | Cozzette et al. | |
| 5,064,619 A | 11/1991 | Finlan | |
| 5,071,248 A | 12/1991 | Tiefenthaler et al. | |
| 5,075,077 A | 12/1991 | Durley, III et al. | |
| 5,076,094 A | 12/1991 | Frye et al. | |
| 5,089,387 A | 2/1992 | Tsay et al. | |
| 5,096,671 A | 3/1992 | Kane et al. | |
| 5,100,238 A * | 3/1992 | Nailor et al. | 356/246 |
| 5,114,676 A | 5/1992 | Leiner et al. | |
| 5,120,662 A | 6/1992 | Chan et al. | |
| 5,134,057 A | 7/1992 | Kuypers et al. | |
| 5,143,854 A | 9/1992 | Pirrung et al. | |
| 5,152,758 A | 10/1992 | Kaetsu et al. | |
| 5,155,791 A | 10/1992 | Hsiung | |
| 5,166,079 A | 11/1992 | Blackwood et al. | |
| 5,182,135 A | 1/1993 | Giesecke et al. | |
| 5,189,902 A | 3/1993 | Groeninger | |
| 5,196,350 A * | 3/1993 | Backman et al. | 436/501 |
| 5,200,084 A | 4/1993 | Liberti et al. | |
| 5,208,535 A | 5/1993 | Nakayama et al. | |
| 5,235,238 A | 8/1993 | Nomura et al. | |
| 5,242,828 A | 9/1993 | Bergstrom et al. | |
| 5,268,306 A | 12/1993 | Berger et al. | |
| 5,280,548 A | 1/1994 | Atwater et al. | |
| 5,304,293 A | 4/1994 | Tierney et al. | |
| 5,305,054 A | 4/1994 | Suzuki et al. | |
| 5,310,686 A | 5/1994 | Sawyers et al. | |
| 5,316,727 A | 5/1994 | Suzuki et al. | |
| 5,321,492 A | 6/1994 | Detwiler et al. | |
| 5,327,225 A | 7/1994 | Bender et al. | |
| 5,334,303 A | 8/1994 | Muramatsu et al. | |
| 5,352,582 A | 10/1994 | Lichtenwalter et al. | |
| 5,356,782 A | 10/1994 | Moorman et al. | |
| 5,369,717 A | 11/1994 | Attridge | |
| 5,374,563 A | 12/1994 | Maule | |
| 5,376,255 A | 12/1994 | Gumbrecht et al. | |
| 5,402,075 A | 3/1995 | Lu et al. | |
| 5,404,756 A | 4/1995 | Briggs et al. | |
| 5,415,842 A | 5/1995 | Maule | |
| 5,418,136 A | 5/1995 | Miller et al. | |
| 5,424,219 A | 6/1995 | Jirikowski | |
| 5,424,220 A | 6/1995 | Goerlach-Graw et al. | |
| 5,430,815 A | 7/1995 | Shen et al. | |
| 5,436,161 A | 7/1995 | Bergstrom et al. | |
| 5,451,683 A | 9/1995 | Barrett et al. | |
| 5,455,178 A | 10/1995 | Fattinger | |
| 5,455,475 A | 10/1995 | Josse et al. | |
| 5,468,236 A | 11/1995 | Everhart et al. | |
| 5,468,606 A | 11/1995 | Bogart et al. | |
| 5,478,527 A | 12/1995 | Gustafson et al. | |
| 5,482,830 A | 1/1996 | Bogart et al. | |
| 5,482,867 A | 1/1996 | Barrett et al. | |
| 5,489,678 A | 2/1996 | Fodor et al. | |
| 5,489,988 A | 2/1996 | Ackley et al. | |
| 5,492,840 A | 2/1996 | Malmqvist et al. | |
| 5,496,701 A | 3/1996 | Pollard-Knight | |
| 5,500,350 A | 3/1996 | Baker et al. | |
| 5,504,013 A | 4/1996 | Senior | |
| 5,510,481 A | 4/1996 | Bednarski et al. | |
| 5,512,131 A | 4/1996 | Kumar et al. | |
| 5,514,501 A | 5/1996 | Tarlov | |
| 5,514,559 A | 5/1996 | Markert-Hahn et al. | |
| 5,518,689 A | 5/1996 | Dosmann et al. | |
| 5,527,711 A | 6/1996 | Tom-Moy et al. | |
| 5,554,541 A | 9/1996 | Malmqvist et al. | |
| 5,569,608 A | 10/1996 | Sommer | |
| 5,571,684 A | 11/1996 | Lawrence et al. | |
| 5,580,697 A | 12/1996 | Keana et al. | |
| 5,599,668 A | 2/1997 | Stimpson et al. | |
| 5,620,850 A | 4/1997 | Bamdad et al. | |
| 5,643,681 A | 7/1997 | Voorhees et al. | |
| 5,658,443 A | 8/1997 | Yamamoto et al. | |
| 5,672,256 A | 9/1997 | Yee | |
| 5,677,196 A | 10/1997 | Herron et al. | |
| 5,717,453 A | 2/1998 | Wohlstadter | |
| 5,736,188 A | 4/1998 | Alcock et al. | |
| 5,738,825 A * | 4/1998 | Rudigier et al. | 422/82.11 |
| 5,753,517 A | 5/1998 | Brooks et al. | |
| 5,780,251 A | 7/1998 | Klainer et al. | |
| 5,795,470 A | 8/1998 | Wang et al. | |
| 5,795,543 A | 8/1998 | Poto et al. | |
| 5,814,565 A | 9/1998 | Reichert et al. | |
| 5,827,748 A | 10/1998 | Golden | |
| 5,834,226 A | 11/1998 | Maupin | |
| 5,837,546 A | 11/1998 | Allen et al. | |
| 5,843,651 A | 12/1998 | Stimpson et al. | |
| 5,849,208 A | 12/1998 | Hayes et al. | |
| 5,852,229 A | 12/1998 | Josse et al. | |
| 5,891,658 A | 4/1999 | Klainer et al. | |
| 5,922,537 A | 7/1999 | Ewart et al. | |
| 5,922,550 A | 7/1999 | Everhart et al. | |
| 5,951,492 A | 9/1999 | Douglas et al. | |
| 5,972,199 A | 10/1999 | Heller et al. | |
| 6,020,047 A | 2/2000 | Everhart | |
| 6,027,944 A | 2/2000 | Robinson et al. | |
| 6,048,623 A | 4/2000 | Everhart et al. | |
| 6,060,256 A | 5/2000 | Everhart et al. | |
| 6,084,683 A | 7/2000 | Bruno et al. | |
| 6,087,184 A | 7/2000 | Magginetti et al. | |
| 6,117,090 A | 9/2000 | Caillouette | |
| 6,136,549 A | 10/2000 | Feistel | |
| 6,136,611 A | 10/2000 | Saaski et al. | |
| 6,171,780 B1 | 1/2001 | Pham et al. | |
| 6,180,288 B1 | 1/2001 | Everhart et al. | |
| 6,200,765 B1 | 3/2001 | Murphy et al. | |
| 6,221,579 B1 * | 4/2001 | Everhart et al. | 435/5 |
| 6,235,241 B1 | 5/2001 | Catt et al. | |
| 6,235,471 B1 | 5/2001 | Knapp et al. | |
| 6,255,066 B1 | 7/2001 | Louderback | |
| 6,271,040 B1 | 8/2001 | Buechler | |
| 6,274,326 B1 | 8/2001 | Stoughton | |
| 6,274,384 B1 | 8/2001 | Starzl et al. | |
| 6,287,783 B1 | 9/2001 | Maynard et al. | |
| 6,287,871 B1 | 9/2001 | Herron et al. | |
| 6,312,961 B1 | 11/2001 | Voirin et al. | |
| 6,331,438 B1 | 12/2001 | Aylott et al. | |
| 6,335,203 B1 | 1/2002 | Patel et al. | |
| 6,395,558 B1 | 5/2002 | Duveneck et al. | |
| 6,399,295 B1 | 6/2002 | Kaylor et al. | |
| 6,423,464 B1 | 7/2002 | Kubo et al. | |
| 6,436,651 B1 * | 8/2002 | Everhart et al. | 435/7.21 |
| 6,436,722 B1 | 8/2002 | Clark et al. | |
| 6,511,814 B1 | 1/2003 | Carpenter | |
| 6,556,299 B1 | 4/2003 | Rushbrooke et al. | |
| 6,573,040 B1 | 6/2003 | Everhart et al. | |
| 6,579,673 B1 | 6/2003 | McGrath et al. | |
| 6,585,939 B1 | 7/2003 | Dapprich | |
| 2002/0025534 A1 | 2/2002 | Goh et al. | |
| 2003/0107740 A1 | 6/2003 | Kaylor et al. | |
| 2003/0119202 A1 | 6/2003 | Kaylor et al. | |
| 2003/0207253 A1 | 11/2003 | Kaylor et al. | |
| 2003/0207254 A1 | 11/2003 | Cohen et al. | |
| 2003/0207255 A1 | 11/2003 | Cohen et al. | |
| 2003/0207256 A1 | 11/2003 | Sayre et al. | |
| 2003/0207257 A1 | 11/2003 | Cohen et al. | |
| 2003/0207258 A1 | 11/2003 | Cohen et al. | |
| 2004/0002110 A1 | 1/2004 | Boga et al. | |
| 2004/0043502 A1 | 3/2004 | Song et al. | |

| | | | |
|---|---|---|---|
| 2004/0063146 A1 | 4/2004 | Sayre et al. | |

FOREIGN PATENT DOCUMENTS

| | | | |
|---|---|---|---|
| EP | 0205698 A1 | 12/1986 | |
| EP | 0453820 A2 | 10/1991 | |
| EP | 0453820 A3 | 10/1991 | |
| EP | 0453820 B1 | 10/1991 | |
| EP | 0469377 A2 | 2/1992 | |
| EP | 0596421 A1 | 5/1994 | |
| EP | 06577737 A2 | 6/1995 | |
| EP | 06577737 A3 | 6/1995 | |
| EP | 0462376 B1 | 7/1996 | |
| EP | 1255111 A1 | 11/2002 | |
| GB | 2 203 542 | 10/1988 | |
| GB | 2 273 772 | 6/1994 | |
| JP | 61 110033 | 5/1986 | |
| JP | 08 261926 | 10/1996 | |
| WO | WO 9301308 A1 | 1/1983 | |
| WO | WO 9005305 | 5/1990 | |
| WO | WO 9105999 | 5/1991 | |
| WO | WO 9403496 | 2/1994 | |
| WO | WO 94/13835 | 6/1994 | |
| WO | WO 9415193 | 7/1994 | |
| WO | WO 96/12962 | 5/1996 | |
| WO | WO 9615193 | 5/1996 | |
| WO | WO 9624062 A1 | 8/1996 | |
| WO | WO 9626435 | 8/1996 | |
| WO | WO 96/29629 | 9/1996 | |
| WO | WO 9633971 | 10/1996 | |
| WO | WO 9810334 | 3/1998 | |
| WO | WO 9827417 | 6/1998 | |
| WO | WO 9843086 A1 | 10/1998 | |
| WO | WO 9931486 A1 | 6/1999 | |
| WO | WO 0019199 A1 | 4/2000 | |
| WO | WO 0036416 A1 | 6/2000 | |
| WO | WO 0050891 A1 | 8/2000 | |
| WO | WO 0065084 A2 | 11/2000 | |
| WO | WO 0065084 A3 | 11/2000 | |
| WO | WO 0065096 A1 | 11/2000 | |
| WO | WO 0065347 A2 | 11/2000 | |
| WO | WO 0065347 A3 | 11/2000 | |
| WO | WO 0065348 A2 | 11/2000 | |
| WO | WO 0065348 A3 | 11/2000 | |
| WO | WO 0078917 A1 | 12/2000 | |
| WO | WO 0138873 A2 | 5/2001 | |
| WO | WO 01/71322 | 9/2001 | |
| WO | WO 01/81921 | 11/2001 | |
| WO | WO 03008971 A2 | 1/2003 | |

OTHER PUBLICATIONS

Abstract of Japanese Patent No. JP2140702.
Abstract of Japanese Patent No. JP2165933.
Abstract of Japanese Patent No. JP2210302.
8 Photographs of Accu-chek® Blood Glucose Meter.
Article —*A conductometric biosensor for biosecurtiy*, Zarini Muhammid-Tahir and Evangelyn C. Alocilja, Biosensors and Bioelectronics 18, 2003, pp. 813-819.
Article —*How to Build a Spectrofluorometer*, Spex Fluorolog 3, Horiba Group, pp. 1-14.
Article —*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.
Article —*One-step all-in-one dry reagent immunoassays with fluorescent europium chelate label and time-resolved fluorometry*, Timo Lögren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.
Article —*Optical Biosensor Assay* (OBA™), Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.
Article —*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.
Article —*Sensing liquid properties with thickness-shear mode resonators*, S. J. Martin, G. C. Frye, and K. O. Wessendorf, Sensors and Actuators A, vol. 44, 1994, pp. 209-218.
Article —*UV Photpatterning Of Alkanethiolate Monolayers Self-Assembled On Gold And Silver*, Americal Chemical Society, 1993.
Bandwidth Market, Ltd. Resource Article.
Evanescent Waves Article.
Pamphlet —The ClearPlan® Easy Fertility Monitor.
Total Internal Reflection Microscopy Article.
U.S. Appl. No. 10/013,937 (KCX-696B), Dec. 11, 2001, Kaylor et al., Systems To View And Analyze The Results From Diffraction-Based Diagnostics.
U.S. Appl. No. 10/718,989 (KCX-741), Nov. 21, 2003, Xuedong Song, Membrane-Based Lateral Flow Assay Devices That Utilize Phosphorescent Detection.

\* cited by examiner

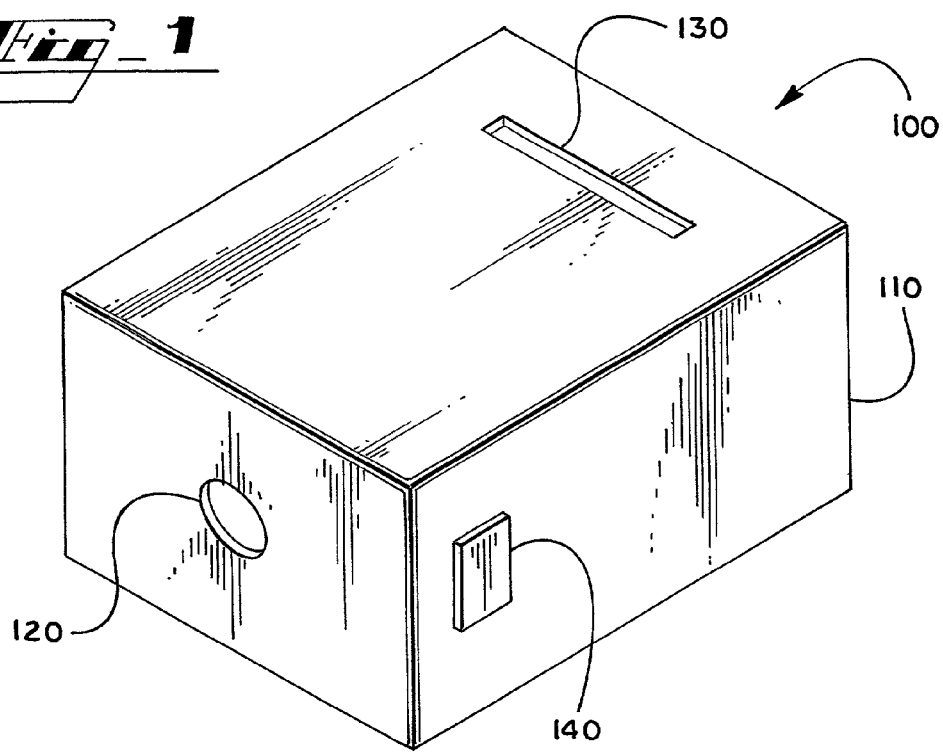
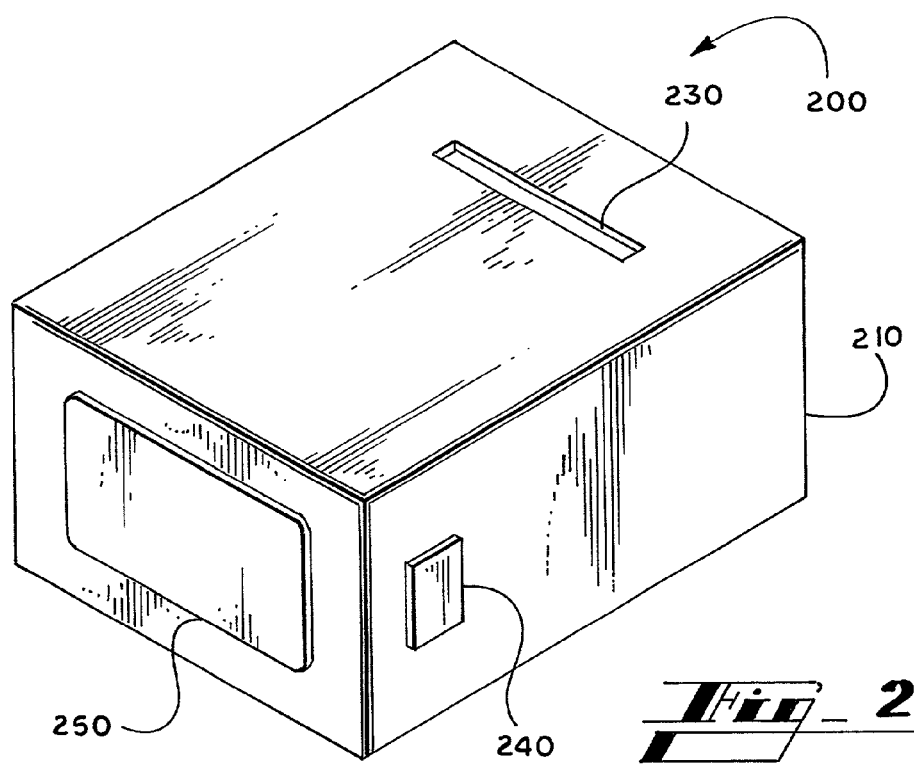

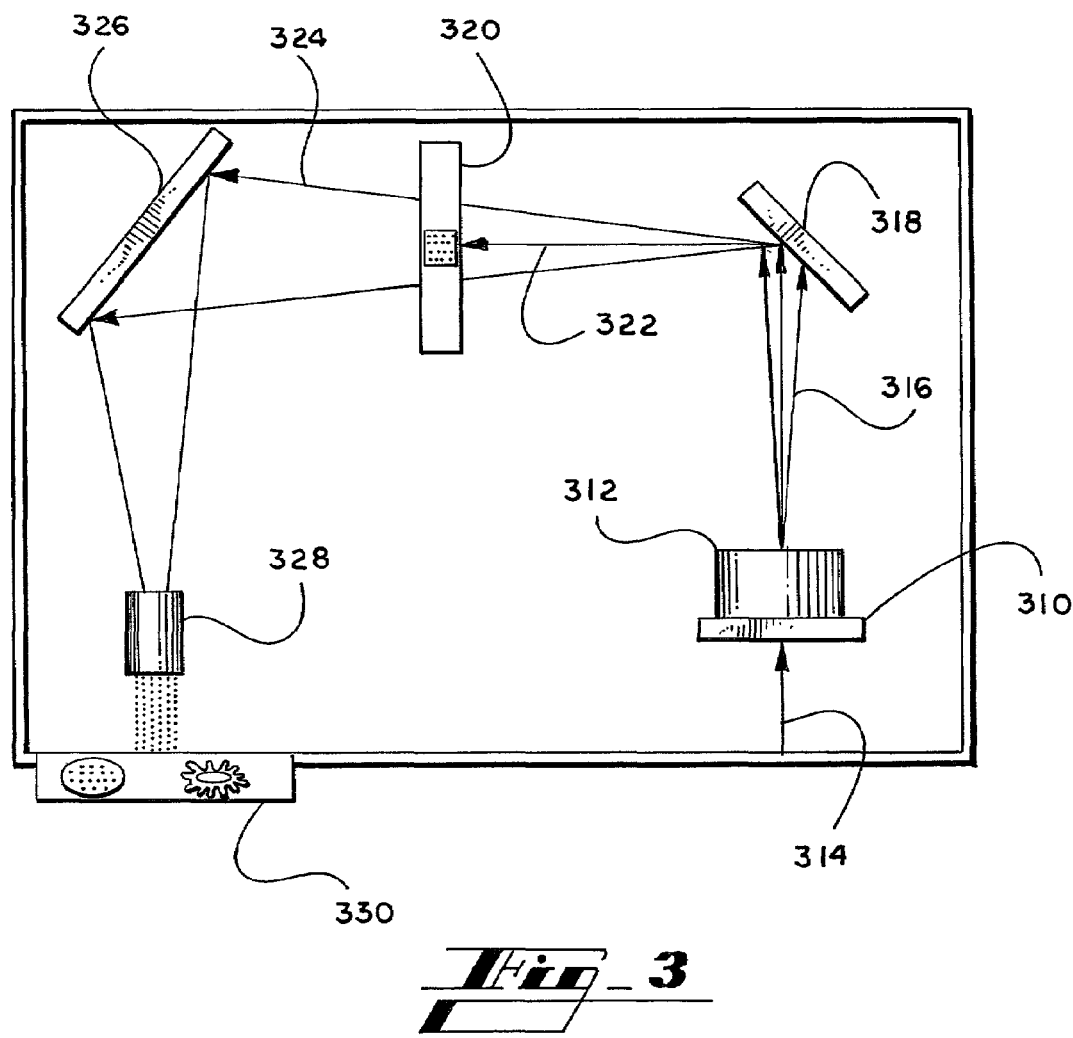
Fig_3

METHODS TO VIEW AND ANALYZE THE RESULTS FROM DIFFRACTION-BASED DIAGNOSTICS

FIELD OF THE INVENTION

The present invention is generally in the field of detecting analytes in a medium and, more particularly, the present invention relates to the methods of viewing and/or analyzing diffraction-based diagnostic devices that are capable of indicating the presence of the analyte in a medium.

BACKGROUND OF THE INVENTION

There are many systems and devices available for detecting a wide variety of analytes in various media. Most of these systems and devices are relatively expensive and require a trained technician to perform the test. There are many cases where it would be advantageous to be able to rapidly and inexpensively determine if an analyte were present. What is needed is a system that is easy and inexpensive to manufacture and is capable of reliable and sensitive detection of analytes.

Sandstrom et al., 24 *Applied Optics* 472, 1985, describe use of an optical substrate of silicon with a layer of silicon monoxide and a layer of silicon formed as dielectric films. They indicate that a change in film thickness changes the properties of the optical substrate to produce different colors related to the thickness of the film. The thickness of the film is related to the color observed and a film provided on top of an optical substrate may produce a visible color change. The authors indicate that a mathematical model can be used to quantitate the color change, and that "calculations performed using the computer model show that very little can be gained in optical performance from using a multilayer structure . . . but a biolayer on the surface changes the reflection of such structures very little since the optical properties are determined mainly by the interfaces inside the multilayer structure. The most sensitive system for detection of biolayers is a single layer coating, while in most other applications performance can be improved by additional dielectric layers."

Sandstrom et al., go on to indicate that slides formed from metal oxides on metal have certain drawbacks, and that the presence of metal ions can also be harmful in many biochemical applications. They indicate that the ideal top dielectric film is a 2–3 nm thickness of silicon dioxide which is formed spontaneously when silicon monoxide layer is deposited in ambient atmosphere, and that a 70–95 nm layer silicon dioxide on a 40–60 nm layer of silicon monoxide can be used on a glass or plastic substrate. They also describe formation of a wedge of silicon monoxide by selective etching of the silicon monoxide, treatment of the silicon dioxide surface with dichlorodimethylsilane, and application of a biolayer of antigen and antibody. From this wedge construction they were able to determine film thickness with an ellipsometer, and note that the "maximum contrast was found in the region about 65 nm where the interference color changed from purple to blue."

U.S. Pat. No. 5,512,131 issued to Kumar et al. describes a device that includes a polymer substrate having a metal coating. An analyte-specific receptor layer is stamped on the coated substrate. The device is used in a process for stamping or as a switch. A diffraction image is generated when an analyte binds to the device. A visualization device, such as a spectrometer, is then used to determine the presence of the diffraction image.

However, the device described by Kumar et al. has several disadvantages. One disadvantage is that a complex visualization apparatus is needed to view any diffraction image.

U.S. Pat. No. 5,482,830 to Bogart, et al., describes a device that includes a substrate which has an optically active surface exhibiting a first color in response to light impinging thereon. This first color is defined as a spectral distribution of the emanating light. The substrate also exhibits a second color which is different from the first color (by having a combination of wavelengths of light which differ from that combination present in the first color, or having a different spectral distribution). The second color is exhibited in response to the same light when the analyte is present on the surface. The change from one color to another can be measured either by use of an instrument, or by eye. Such sensitive detection is an advance over the devices described by Sandstrom and Nygren, supra, and allow use of the devices in commercially viable and competitive manner.

However, the method and device described in the Bogart, et al. patent has several disadvantages. One disadvantage is the high cost of the device. Another problem with the device is the difficulty in controlling the various layers that are placed on the wafer so that one obtains a reliable reading.

Patent WO 94/13835, issued to Bogdanski et al., describes a method and system for detecting macromolecules. The system includes a probe that is a former of predetermined dimensions such that it diffracts light in a known pattern. Upon binding by a macromolecule (e.g., analyte), the position of the diffraction peaks will change due to this binding.

Thus, the system must include a more complex detector and analyzer to detect changes in a diffraction pattern. In comparison, the current diffraction-based system described is detecting the formation of a diffraction pattern or image, so that only the appearance of diffracted light must be detected. Therefore, one disadvantage of the method and system described by Bogdanski et al. is that a more complex apparatus is needed to detect changes in the diffraction pattern. Another disadvantage is the more complex methods required to prepare the probe, which involve multiple steps with photoresist and/or etching steps conducted on a brittle, silicon dioxide surface; these methods are not amenable for a full-scale manufacturing process due to high scale capital costs.

U.S. Pat. No. 5,196,350 to Backman, et al., describes an optical detection method that uses an immunoassay device along with a mask that produces a diffraction pattern. The immunoassay device is placed between the mask and light source, so that binding by the analyte causes a change in the diffraction or interference pattern caused by the mask. Thus, this patent has similar disadvantages as the Bogdanski patent since it uses a method based on detecting changes in a diffraction pattern, rather than formation of one, due to binding. This makes analysis more complex, since these changes are more subtle than a simple yes/no of a diffraction image being formed in the presence of an analyte.

U.S. Pat. No. 4,992,385 to Godfrey, et al., describes a method to prepare a diffraction grating with a thin polymer film, for subsequent use as a sensing device. The sensing device then requires the use of a spectrophotometric technique during the assay to detect changes in its optical properties due to analyte binding. Thus, as with the previous two patents, this patent also involves a more complex detection method since it must detect changes in a diffraction pattern, rather than simple formation of a pattern due to the analyte.

Some commercial lateral flow technologies have been used which employ latex bead technology. These technologies are currently employed in many of the commercially-available home diagnostic kits (e.g. pregnancy and ovulation kits). These kits use colored beads which accumulate in a defined "capture zone" until the amount of beads becomes visible to the unaided eye. However, these systems lack the requisite sensitivity to test for many analytes, since a much larger number of latex beads must bind in the capture zone to be visible to the naked eye than that required to cause diffraction in the same size zone. Theoretically, the number of beads needed is about 2 to 3 orders of magnitude higher than the number of beads required by the sensors of the present invention.

There have been several novel inventions directed to the use of biosensing devices to detect analytes. Some of these biosensors have a self-assembling monolayer and have been used to detect analytes. These types of devices are set forth in U.S. Pat. Nos. 5,922,550 and 6,060,256. Other devices having a self-assembling monolayer and using microparticle technology have been used to detect smaller analytes and are set forth in U.S. Pat. No. 6,221,579 B1. Finally, some sensing devices have been provided that incorporate non-self-assembling materials and again provide a diffraction image that can be seen with an unaided eye. This type of device is set forth in U.S. patent application Ser. No. 09/213,713. However, the present invention enhances the ease-of-use and/or accuracy of these biosensing devices by generally providing a faster, more accurate interpretation of the results of these devices.

Accordingly, what is needed is an analyzer that may be used with various diffraction-based diagnostic systems to help determine the presence of an analyte in a quick and accurate manner. Also what is needed is a method of using this analyzer to quickly and accurately determine the presence of an analyte in a given sample.

BRIEF SUMMARY OF THE PRESENT INVENTION

The present invention provides a system and method for viewing and/or analyzing the results from diffraction-based diagnostic systems that are quicker, more accurate and/or simpler to use than methods and systems requiring complex visualization devices. The present invention may be used with a variety of different diagnostic systems and methods to enhance the effectiveness and/or usefulness of these devices in detecting smaller analytes that may not have been detected using the diagnostic system alone.

Accordingly, it is one desire of the present invention to provide a method of viewing and/or analyzing results from a diffraction-based diagnostic system.

The present invention also desirably provides a system for viewing and/or analyzing results from a diffraction-based diagnostic system.

Desirably, the present invention also provides a method of viewing and/or analyzing results from a diffraction-based diagnostic system using a device that provides results that are independent of the user's eyesight.

Additionally, the present invention desirably provides a method of viewing and/or analyzing results from a diffraction-based diagnostic system that provides accurate results in a timely manner and reduces error.

The present invention also desirably provides a method of viewing and/or analyzing results from a diffraction-based diagnostic system that may be automatically controlled.

Desirably, the present invention also provides a system of viewing and/or analyzing results from a diffraction-based diagnostic system using an analyzer that is able to store past results in memory, thereby permitting the user to recall the results of the more recent samples.

Additionally, the present invention desirably provides a system of viewing and/or analyzing results from a diffraction-based diagnostic system that permits remote data access.

The present invention accomplishes at least one of these goals by providing a novel viewer and/or analyzer that may be used in conjunction with diffraction-based diagnostic systems to determine the presence of an analyte in a given sample. The viewer and/or analyzer may be used to determine the presence of an analyte in a sample by viewing and/or analyzing whether a diffraction image has been generated by the analyte when introduced with the diagnostic system.

Additionally, the viewer and/or analyzer may be used for quantitative or semi-quantitative analyses. The devices described in the above-referenced documents can be produced by printing a species that will bind, react or otherwise associate with an analyte of interest onto a surface and is referred to herein as a "binder". The species that binds, reacts or otherwise associates with an analyte of interest is referred to as a binder and may include any chemical species, compound, composition, moiety, particle etc. that will bind, react or otherwise associate with the analyte of interest.

Preferably, the binder is specific to the analyte of interest or a class of analytes of interest and does not appreciably bind, react or otherwise associate with other species that may be found in the sample of interest.

Generally, the binder is printed onto a substrate, for example a plastic film, in a defined pattern such that the binder-printed film does not diffract electromagnetic radiation when the electromagnetic radiation is reflected off of or transmitted through the binder-printed film but diffracts electromagnetic radiation after the binder-printed film is exposed to the analyte and the analyte has bound, reacted or otherwise associated with the binder. Alternatively, the binder-printed film or surface may exhibit a measurable increase or decrease in diffraction after exposure to the analyte. For example, a film may be printed with a binder such that binder-printed film initially diffracts light does but does diffract light or diffracts less when an analyte binds, associates or otherwise reacts with the binder-printed surface. In another example, the film may be printed with a binder such that binder-printed film initially diffracts light does but diffracts light to a measurably greater extent when an analyte binds, associates or otherwise reacts with the binder-printed surface. The presence of analyte can be determined by a measurable change in diffraction of light that is transmitted through or reflected off of the substrate surface.

Generally, an analyte may be any stimulus including but not limited to any chemical or biological species, compound, composition, moiety, particle, etc that that will bind, react or otherwise associate with the binder or with which the binder will respond. Analytes that are contemplated as being detected include but are not limited to the following: bacteria; yeasts; fungi; viruses; protozoa; or antigens specific to these microbes; rheumatoid factor; antibodies, including, but not limited to IgG, IgM, IgA and IgE antibodies; carcinoembryonic antigen; *streptococcus* Group A antigen; viral antigens; antigens associated with autoimmune disease; allergens; tumor antigens; *streptococcus* Group B antigen; HIV I or HIV II antigen; or host response (antibodies) to these and other viruses; antigens specific to RSV or host response (antibodies) to the virus; an antigen;

enzyme; hormone; polysaccharide; protein; lipid; carbohydrate; drug or nucleic acid; *Salmonella* species; *Candida* species, including, but not limited to *Candida albicans* and *Candida tropicalis; Salmonella* species; *Neisseria meningitides* groups A, B, C, Y and W sub 135, *Streptococcus pneumoniae, E. coli* K1, *Haemophilus influenza* type B; an antigen derived from microorganisms; a hapten, a drug of abuse; a therapeutic drug; an environmental agent; antigens specific to Hepatitis and so forth.

BRIEF DESCRIPTION OF THE DRAWINGS

FIG. 1 is a perspective view of a viewer according to one embodiment of the present invention.

FIG. 2 is a perspective view of a viewer according to another embodiment of the present invention.

FIG. 3 is a schematic of an analyzer according to one embodiment of the present invention.

DETAILED DESCRIPTION OF THE INVENTION

Figure 4:
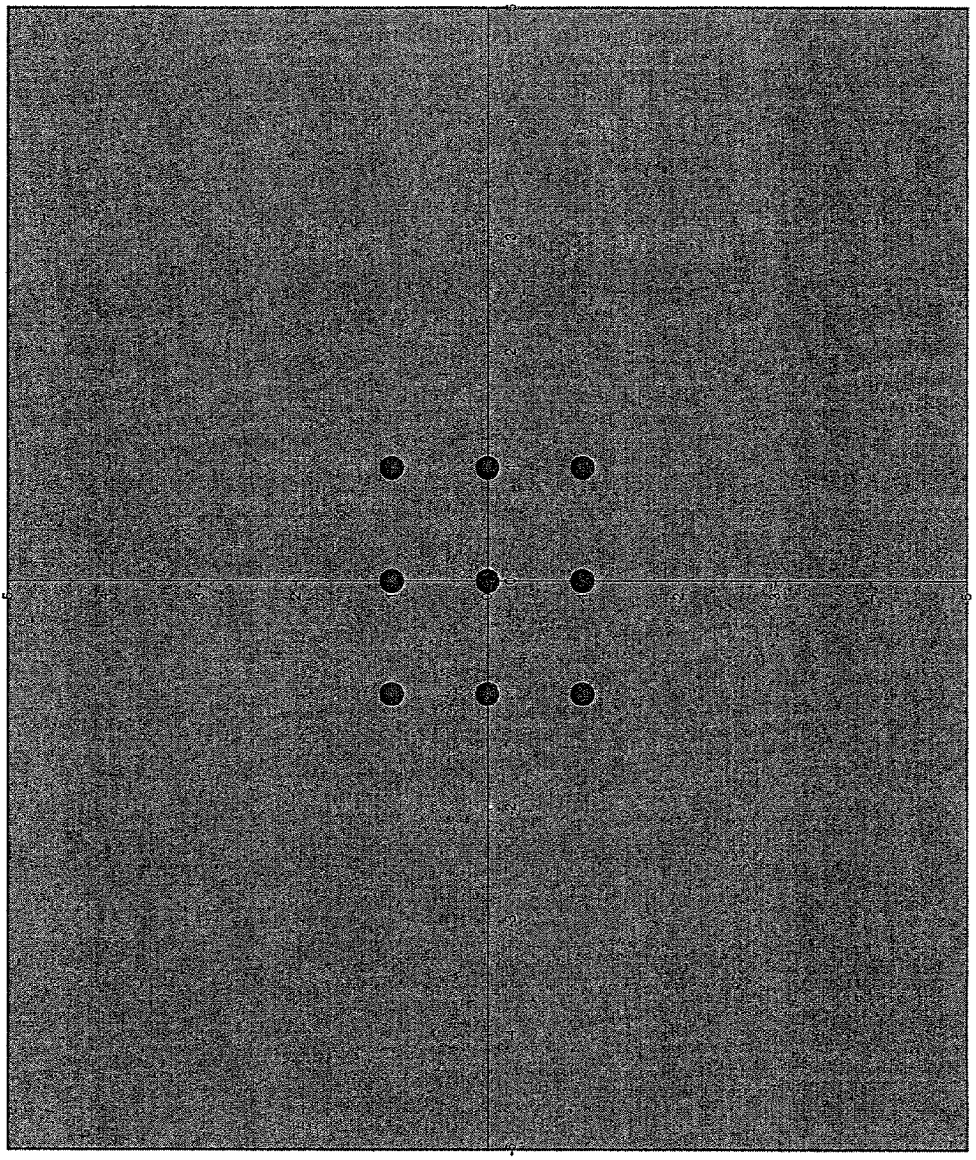
FIG. 4 is a schematic of a mask useful to measure light intensity of the zero and first order from a diffraction image that is an x,y array.
Figure 5:
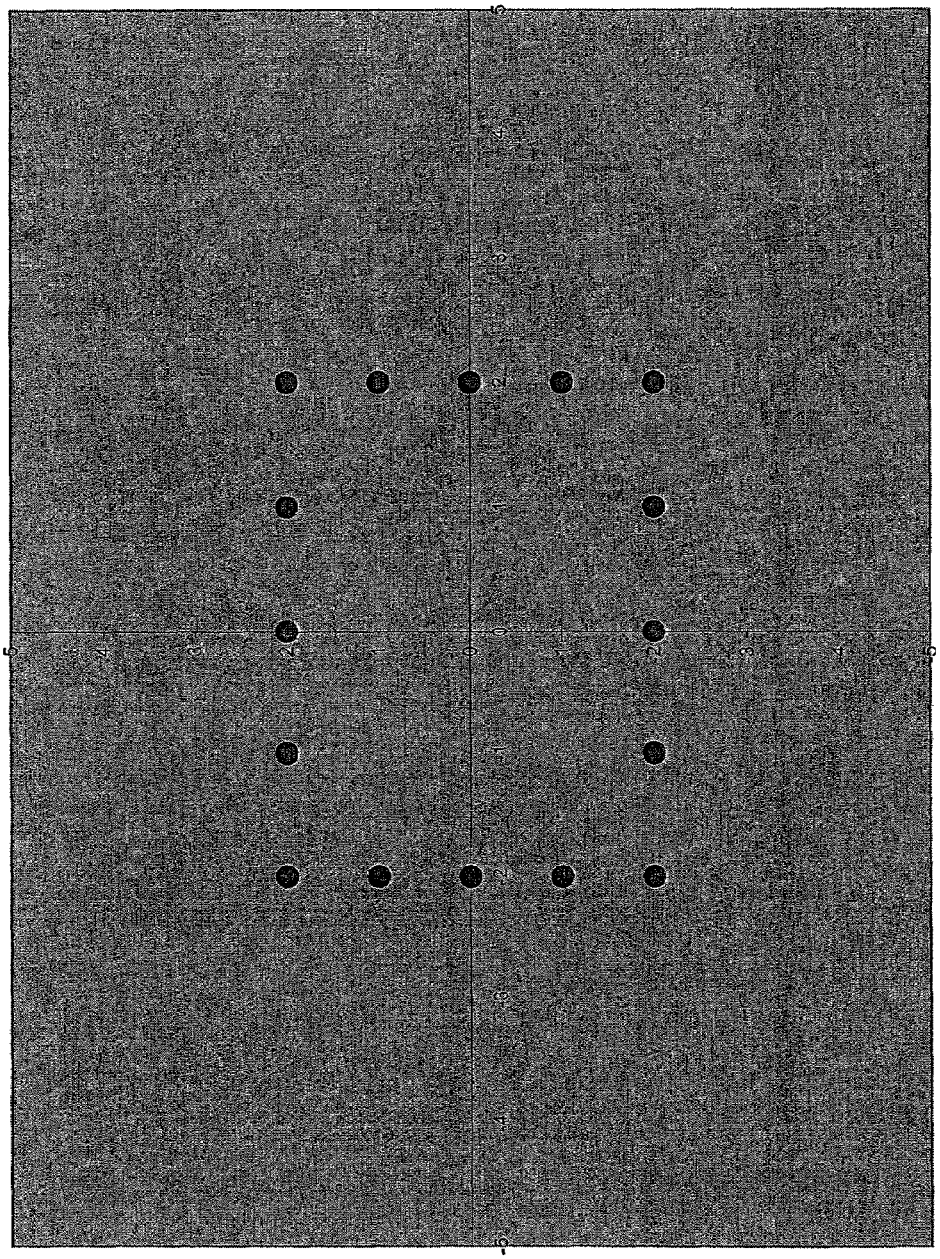
FIG. 5 is a schematic of a mask useful to measure light intensity of the second order from a diffraction image that is an x,y array.
Figure 6:
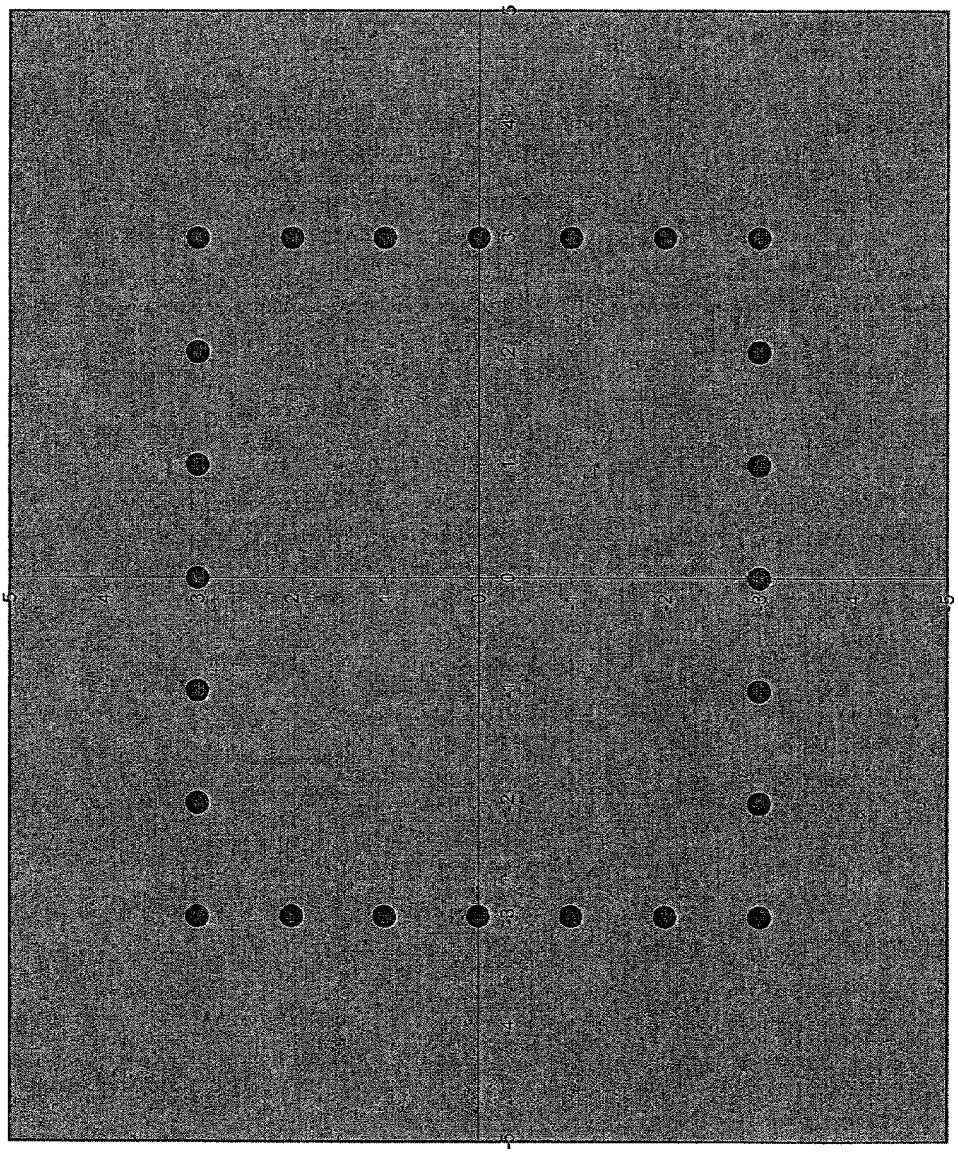
FIG. 6 is a schematic of a mask useful to measure light intensity of the third order from a diffraction image that is an x,y array.
Figure 7:
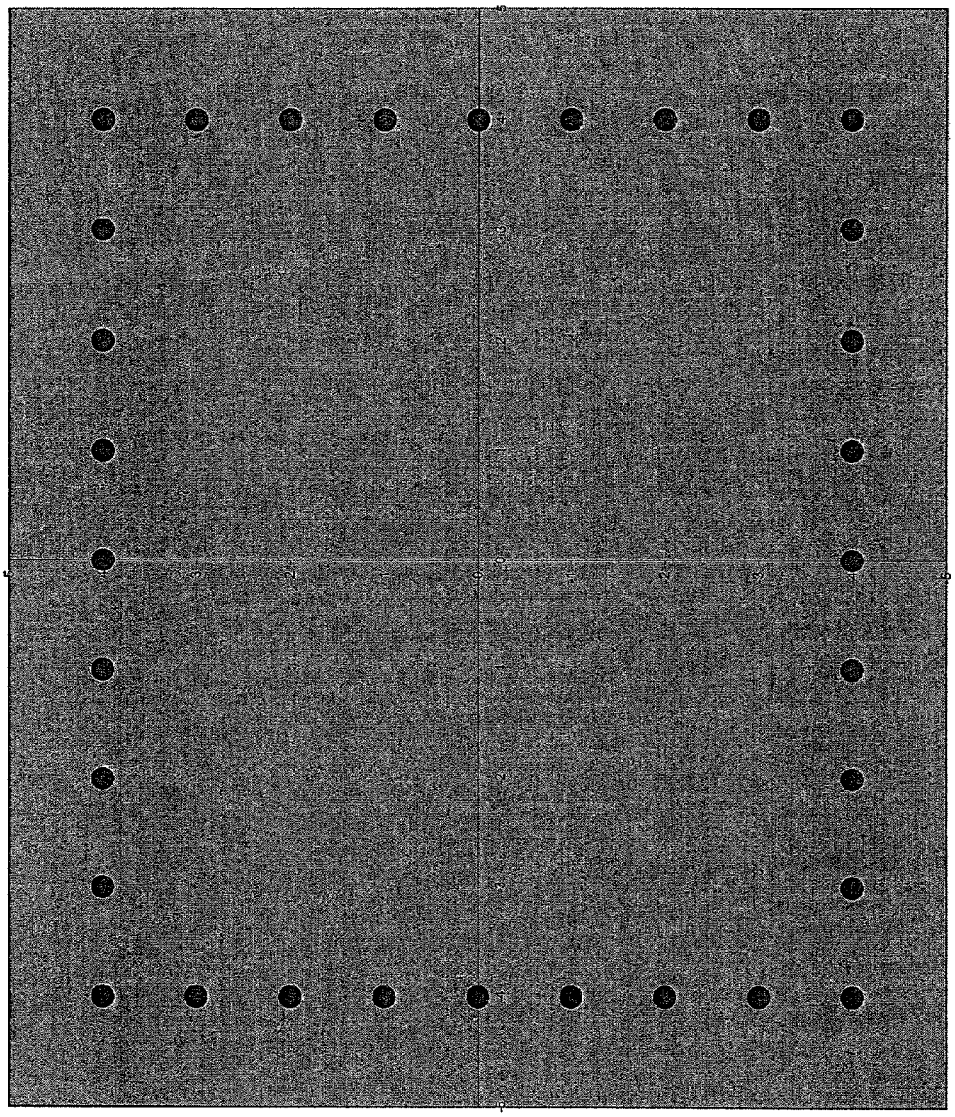
FIG. 7 is a schematic of a mask useful to measure light intensity of the fourth order from a diffraction image that is an x,y array.

The present invention provides an analyzer, system and method for viewing and/or analyzing the results from diffraction-based diagnostic systems. The present invention may be used with a variety of different diagnostic devices and systems to enhance the effectiveness and/or usefulness of these devices by detecting analytes quickly and accurately, while doing so in a method that provides ease-of-use to the user.

The present invention first provides a viewer that uses a light source to transmit or reflect light through a sample that has been connected with the viewer. If an analyte has bound to the diffraction-based sensing device, the transmitted or reflected light will generate a diffraction image or pattern. This image may be seen directly with an unaided eye. Or the image may be projected against a screen that permits the user to determine whether diffraction has occurred.

The present invention also provides an analyzer that uses an algorithm or series of algorithms and/or computer software to analyze a diffraction-based sensing device to determine whether an analyte or analytes are present on the sensing device and, therefore, present in a sample that is being tested. While the diffraction-based sensing device may be used without the analyzer, the analyzer desirably provides results more quickly, more easily and/or more accurately than without the use of the analyzer.

The algorithm or algorithms used are developed based upon the parameters of the system in which the analyzer will be used. Additionally, if a software element is used, it may be adjusted as needed such that the analyzer becomes simpler and/or more accurate in determining whether the analyte is present in the sample.

The analyzer desirably converts the diffraction image from a sample into a yes/no result for the user. Thus, the user would not necessarily see the diffraction image, but would see a display giving the interpretation: e.g., "analyte present", "analyte not present", or "error". Options for the analyzer include audible tone generators, illuminated lamps, LEDs, or LCD displays to indicate the results; a printer to provide a printout of results; memory to store previous results; or other functions such as heating or mixing that may be employed to enhance test results, reliability, and/or convenience, among others.

In addition to the viewer and/or analyzer, the present invention also includes a method for detecting an analyte using a viewer and/or analyzer. As discussed, the analyzer may use an algorithm or algorithms and/or a software element to determine the presence of the analyte in a given sample.

Also, the present invention includes a system for detecting an analyte using a diffraction-based sensing device and a viewer or an analyzer. As discussed, the analyzer may use an algorithm or algorithms and/or a software element to determine the presence of the analyte in a given sample.

The present invention also includes a replacement to the complex prior art visualization devices, such as spectrometers, that had been used in some diffraction-based systems. Rather than requiring the user to use a complex visualization device, such as a spectrometer, the present invention uses a simple viewer that enables the user to see the diffraction image or an analyzer that displays an easy to interpret signal depending on whether the analyte is present, providing easy interpretation of results. The analyzer device works by using a means to collect light from diffracting samples; if enough light is diffracted, this triggers the device to indicate the presence of an analyte. The small device may also increase accuracy since it provides the ability to calibrate results such that false positives can be reduced. This may be accomplished by designing the unit so that it blocks out weakly diffracting signals, as seen with some controls. Thus, more highly diffracting, true positives are detected.

The present invention is based upon the use of diffraction-based sensing devices. In both the system and methods of the present invention, the analyzer is contemplated being used with these diffraction based sensing devices to expand upon the usefulness of these devices. There are large numbers and types of diffraction-based sensing devices and it is contemplated that the analyzers of the present invention may be used with any of these diffraction based sensing devices.

As used herein, a "diffraction-based sensing device" is meant to include any sensing device that, upon binding of an analyte with the device, will diffract transmitted or reflected light to form a diffraction image. The diffraction-based sensing device preferably does not diffract light if the analyte is not present, but does diffract light when the analyte is present. Those skilled in the art will recognize that measurement in the difference between two or more diffraction images may also be used to detect the presence of an analyte in the present invention. Those skilled in the art will also recognize that the diffraction-based sensing device may include a first, diffracting image and, after the analyte has bound to the device, a second-non-diffracting image.

The diffraction-based sensing devices useful in the present invention generally provide a substrate upon which is placed a material that binds to the analyte of choice. Other features may be provided to enhance the effectiveness of the diffraction-based sensing devices such as additional coatings, blocking layers, diffraction enhancing elements and so forth.

Accordingly, one aspect of the present invention includes a viewer that allows a user to easily interpret whether an analyte is present in a system by permitting the user to see whether a diffraction image is present. The viewer generally includes a means for holding the diffraction-based sensing device, a means for transmitting or reflecting a light through the sensing device and, possibly, a housing for holding the holding means and the light transmitting means. The viewer may also include means for activating the light, and means for more easily determining whether a diffraction image is present, such as a projection screen.

FIGS. 1 and 2 illustrate two possible embodiments of a viewer according to the present invention. In FIG. 1, the viewer 100 includes a housing 110 that includes a light source (not shown). The light source may be a laser light, LED, a light bulb, or any other means capable of generating a light. The housing includes a hole 120 through which the user may look. The housing 110 includes a slot 130, or other means, into which the sample to be viewed is placed. The sample may also be held in place using a clamp, tray or other suitable means. When the sample is placed into the slot 130, the light source may automatically be activated, or a button 140 or other means may be used to activate the light source. The light is then either transmitted or reflected through the sample. The user of the device may then simply look through the hole 120. If the analyte is present, the user will see a diffraction image, and if the analyte is not present, then the user will see just the light source.

FIG. 2 illustrates an alternative embodiment of a viewer according to the present invention. The viewer 200 includes a housing 210, a light source (not shown) and a slot 230 or other means for holding the sample, along with a button 240 or other means for activating the light source. However, instead of the hole 120 used in FIG. 1, the viewer 200 includes a screen 250 against which the transmitted or reflected light is projected. In use, the light source is activated and the light is then either transmitted through or reflected off the sample. If the analyte is present, the user will see a diffraction image projected against the screen 250, and if the analyte is not present, then the user will see just the light source projected against the screen 250.

An optional component for the viewers described above would be to use an opaque object (e.g., a mask) to block the zero order or non-diffracted light beam. In this way, a user would only see the diffracted orders if the analyte is present, and would see no light at all if the analyte were not present.

Instead of using a viewer that permits the user to view, with an unaided eye, whether a diffraction image has been generated, the present invention may also provide an analyzer that enables a user of a diffraction-based sensing device to more quickly and efficiently ascertain the presence of an analyte in a given sample. While the user of the diffraction-based sensing device may be able to determine the presence of an analyte using an unaided eye and a viewer, the analyzer is intended to either confirm the determination made by the user, or be used to make the initial determination with the user possibly confirming with an unaided eye, depending on the abilities of the user and/or the type of diffraction image generated.

If the analyzer is used alone or is used in making an initial determination of the presence of the analyte in the sample, then diffraction algorithms will generally be used to set the standards by which a positive result, indicating the presence of the analyte, is determined or a negative result, indicating the lack of the presence of the analyte, is determined. The type of algorithm used may be based upon a variety of factors, either alone or in combination and including, but not limited to, the analyte to be detected, the type of diffraction-based sensing device used, the sample to be tested, the diffraction image generated, the size of the features in the diffraction image, the diffraction image and/or feature sizes and/or shapes in that pattern, the type of analyzer used, the desired level of sensitivity, and the overall system in which the device is used, among others. Accordingly, the algorithms provided herein are meant only to be representative examples of algorithms that may be used in the present invention. It is anticipated that other algorithms may be used as long as they are capable of determining the presence of an analyte using a diffraction-based sensing device in an accurate and reliable manner. Additionally, it is desired that the algorithms are able to quickly determine the presence of the analyte, though adequate accuracy is more desirable.

The structure of the analyzer may vary in view of one or more factors including, but not limited to, the analyte to be detected, the type of diffraction-based sensing device used, the sample to be tested, the diffraction image generated, the desired level of sensitivity, and the overall system in which the device is used, among others. Generally, the analyzer includes a housing to contain the internal components, a means for illuminating the diffraction-based sensing device in a manner that generates a diffraction image, a means for measuring the amount of diffracted and/or non-diffracted light, a means for converting the measurement from the means for measuring the amount of diffracted light to a result indicating the presence or lack of the analyte, and/or a means for informing a user whether the analyte is present in the sample.

The means for illuminating the diffraction-based sensing device in a manner that generates a diffraction image may include a light source or some related illumination sources. Desirably, a light source is used. The light source may be internal (LED, laser diode, or halogen lamp, for example) or external (ambient light, for example) to the housing. Additionally, the light source may be in the visible spectrum or invisible to the human eye. The light source is chosen such that the analyzer is capable of detecting whether diffraction of the light source has occurred due to the presence of the analyte on the diffraction-based sensing device. It is contemplated that an LED, a laser, or any focused light source will be the most useful light sources in the present invention, though other light sources may be used. Additionally, the light source may be transmitted directly through the diffraction-based sensing device, or the light from the light source is illuminated on the surface of the device, usually at an angle, such that the diffraction image is reflected off the surface.

The analyzer may employ one or more photodetectors as the means for measuring the amount of diffracted and/or non-diffracted light. Possible photodetectors include photovoltaic or photoconducting semiconductor junctions (photodiode), bolometers, or pyroelectric detectors. Detectors may be arranged individually or in multiplexed arrays (such as charge coupled devices or CMOS interfaced detector arrays).

In a desirable embodiment, the analyzer incorporates a microprocessor or similar device as a means for converting the measurement from the means for measuring the amount of diffracted light to a result indicating the presence or lack of the analyte.

Once a result, either positive or negative has been determined, this result may be indicated to the user through a means for informing a user whether the analyte is present in the sample. This means preferably comprises a display or similar means capable of informing the user. The display may be any standard display, such as a liquid crystal display (LCD). The display could possibly show the diffraction image, thereby allowing the user to see whether diffraction had occurred. Or, the display could simply provide a message, such as "yes" or "no" or "analyte present" or "analyte not present" or some similar message to let the user know whether the analyte was present in the sample without the user having to interpret whether diffraction had occurred, thereby reducing human error. In yet another embodiment, in the event of an error or if the analyzer is unable to determine the presence of the analyte, then a message to this effect may be displayed.

Alternatively, at least one light may be used to signal whether the analyte was present. For example, one light may be used and the light would illuminate only when the analyte was present or not present, depending on the desired set-up. Alternatively, two or more lights may be used with one light labeled "yes" and another light labeled "no" and the analyzer would illuminate the appropriate light. Or the lights could be color coded such that one color, such as green, could be used to indicate that the analyte was present while a second color, such as red, could be used to indicate that the analyte was not present.

The analyzer may further include one or more additional features to assist the user in more accurately and/or quickly determining the presence of the analyte. For example, the analyzer may include a means for holding the sample in place such that a more accurate result may be obtained or to more quickly determine whether the analyte is present. The means may include a tray, a clamp, a slot, or any other similar means capable of holding the sample in place.

The analyzer may also include means for directing, focusing and/or intensifying the light source. The means may reflect the light, as discussed previously, or may intensify the light, thereby increasing the level of diffraction and, therefore, increasing the sensitivity and/or accuracy of the device. The means for directing and/or intensifying the light may include mirrors and/or lenses or any similar means. By using these types of means, it may be possible to avoid using a microprocessor or the like as the enhanced light diffraction may permit a user to determine the presence of the analyte with an unaided eye.

Additionally, the present invention may use a mask to help eliminate the possibility of a false positive as a result of the photodiode detecting diffused or scattered light instead of diffracted light when light is passed through or reflected from the sensing device. The mask includes an opaque object that has holes that align with the diffraction image, or alternatively, holes that align to some portion of the diffraction image of interest. The mask may be used to block out all light except the diffracted light from being detected by the means for measuring the amount of diffracted light, such as the photodiode. The mask holder or assembly may also include means for rotating the mask depending on the diffraction-based sensing means used, or for any other desired reason.

In use, the mask is placed between the diffraction-based sensing device and the photodiode, or other means for measuring light. The mask includes a solid portion and holes that permit light to pass through. The pattern of the holes is chosen to correspond to the diffraction image generated by the diffraction-based sensing device if the analyte has bound to the sensing device. As such, the mask blocks out non-diffracting light while letting diffracted light through; in this way, the intensity of only diffracted light can be measured.

Then, the mask is rotated such that diffracted light is blocked, and the amount of light intensity is measured again. Some diffused or scattered light, if present, will pass through the holes in the mask, while the diffracted light will be blocked. As such, when a second light intensity reading is taken, a comparison of the amount of light detected with the mask in place to the amount of light detected when the mask is rotated will determine whether the analyte is present in the sample. The analyzer will compare the readings and, based upon the algorithm used, will provide a result. If a mask is used in the analyzer, the mask may be included in the analyzer housing along with a means for rotating the mask the desired amount to measure both diffracting and non-diffracting light.

If a microprocessor is used as the means for converting the measurement from the photodiode or similar device to a result indicating the presence or lack thereof of the analyte, then the microprocessor may include memory capability to allow the user to be able to recall the last several results from the analyzer. The number of results recalled may vary as desired. Generally, however, the memory would be able to recall at least about five results. Those skilled in the art will appreciate that suitable computer-readable memory devices include RAM, ROM, EPROM, EEPROM, flash memory cards, digital video disks, Bernoulli cartridges, and so forth. Still, any type of computer chip including a memory may be affixed to, or otherwise associated with, the analyzer.

FIG. 3 provides yet another embodiment of an analyzer of the present invention, with this embodiment having several optional features. This embodiment provides a way of directing the light such that it can be used in a compact reader device. As shown in FIG. 3, a sample 310 is placed on a holder 312 for holding the sample 310 in place. A light source 314 is transmitted through the sample 310. If the sample contains the analyte, then light is diffracted and exits the light source as a series of light 316 that includes both diffracted and non-diffracted light. The diffracted light 316 is reflected off a mirror 318 and a mask 320 may be used to block any light 322, which consists essentially of non-diffracted light, that is not diffracted. The remaining light 324, which consists essentially of diffracted light, is again reflected off another mirror 326 and collected by a photodiode 328 and a microprocessor (not shown) interprets the result and provides the appropriate result on the display 330, which is a series of lights for this embodiment.

In one embodiment, a mask 320 is used to block light 322 that is not diffracted. Thus, the mask allows mostly diffracted light into the photodiode, which measures the intensity of light. In yet another embodiment, the measured intensity of light is forwarded to a microprocessor that employs an algorithm. A result from the algorithm is then fed to the display 330, such as a set of lights that could light up as a simple way to indicate to the user whether the sample was positive or negative (e.g., red light=negative; blue or green light=positive). If no light is diffracted, then all of the light would be blocked and the photodiode 328 would detect no light and, therefore, the analyzer would indicate that the analyte is not present in the sample. As such, whether the analyte is present in the system will dictate the amount of light detected by the photodiode 328. However, as some small amount of diffraction might occur in the event of error, such as dust entering the system, the photodiode 328 may detect some light even though the anaylte is not present in the sample 312. Accordingly, when using the analyzer, the degree of diffraction may be taken into account when determining whether the photodiode and microprocessor indicate the presence or lack thereof of the analyte in the sample.

In an optional embodiment, the method to analyze the diffraction samples also uses a mask. However, two measurements are taken of light intensity. The first measurement is of the diffracted light that clears the mask. The mask is then rotated so that diffracted light is blocked; this results in only diffused light, if present, passing through the mask and being measured. The ratio of the two measurements is then used to determine whether a sample is positive ("yes", analyte is present) or negative ("no", analyte is not present). In this way, the method allows for diffused light to be accounted for, such that a "messy" sample, which is defined as a sample that diffuses or scatters light but does not diffract, does not cause a positive reading.

The types of algorithms that may be used are numerous and may vary depending on one or more factors including, but not limited to, the analyte to be detected, the sample used, the components of the analyzer, the degree of sensitivity desired, the system in which the analyzer is used, and others. In one embodiment of the present invention, the desired algorithm for the system will allow the user to manipulate the data (data light intensities diffracted at various diffraction orders) such that only the higher diffracting orders are counted as a diffracting sample. This could increase the accuracy of the system.

The algorithm will have two basic components: 1) the method by which the light intensity is measured and 2) the calculation used to trigger either a "positive" or yes reading versus a "negative" or "no" reading. The algorithm is one of the desired components of the present invention since it provides a way to increase accuracy, especially by eliminating false positives.

An example algorithm could be:

(Intensity of diffracted light at $\geq 2^{nd}$ orders)/(Intensity of incoming light)

In one case, the incoming light could be measured prior to going through the sample. In a desired embodiment, the incoming light was measured after transmitting through the sample and collecting the diffracted and zero order beam for this intensity reading.

The algorithm could set a cutoff value for this ratio such that samples measuring above this value="positive" and samples measuring below this value="negative". One example of a cutoff value would be about 0.3. Again, the cutoff value may vary depending on the analyte to be detected, the type of diffraction-based sensing device used, the sample to be tested, the diffraction image generated, the size of the features in the diffraction image, the diffraction image and/or feature sizes and/or shapes in that pattern, the type of analyzer used, the desired level of sensitivity, and/or the overall system in which the device is used.

Other algorithms may be used and examples of some that may be used are provided in the examples below.

The present invention also includes systems and methods for determining the presence of an analyte in a sample. In these systems and methods, a diffraction based sensing device is used in conjunction with the analyzer. A sample to be tested is placed on the diffraction based sensing device. Depending on the type of diffraction based sensing device used, the sample may need to sit for several minutes to allow time for the analyte, if present, to bind to the diffraction based sensing device. Or, the diffraction based sensing device and sample may be viewed immediately.

Light is then transmitted either directly through or is reflected off the diffraction based sensing device. If the analyte to be detected is present in the sample, then the analyte diffracts light. If the analyte is not present, then light is not diffracted. However, it is contemplated that the diffraction based sensing device could also be constructed and arranged such that light will not diffract if the analyte is present, but will diffract if the analyte is not present. Also, the diffraction based sensing device may be designed such that if the analyte is not present, light will be diffracted in a first amount and if the analyte is present the light will be diffracted in a second amount and the analyzer is capable of measuring the difference and determining whether the analyte is present.

After light has been transmitted or reflected through the sample and diffracted, the diffracted light is measured using a suitable detector, such as a photodiode. The detector measures the intensity of the diffracted light. The detector may optionally measure the intensity of the incident light either before the sample is placed in the instrument or after the sample is removed. Alternately, a second detector and a beam-splitter arrangement may be used to measure the intensity of the incident light at the same time as the diffracted light. Then a means for determining whether the analyte is present, such as a microprocessor, is used to determine whether the sample is positive or negative. If a microprocessor is used, then a code or software program incorporating an algorithm is desirably used to analyze the input from the photodiode. To run the algorithm, a software element may be installed to run through the necessary calculations and ascertain the final result. This result is then provided to the user using a means for informing the user whether the analyte is present in the sample, such as a LCD display or a series of lights.

If a software element is used in the present invention, it desirably provides computer executable instructions for interpreting the amount of light measured by the photodiode and generating an output representing whether the analyte is present in the sample. The microprocessor executes the computer-executable instructions of the software element.

The system also provides an input interface and an output interface. Using the input interface, the microprocessor may receive data relating to amount of light from the photodiode. Using the output interface allows the microprocessor, controlled by the software element, to communicate with the means for informing the user whether the analyte is present in the sample to provide a result to the user.

Those skilled in the art will appreciate that the software element may also be executed by a distinct system, such as a desktop, laptop, or handheld computer system, that is in communication with and operated in conjunction with analyzer.

The diffraction-based sensing devices may include a variety of different features depending on factors previously discussed.

In general, the diffraction based sensing devices will use a substrate. The substrate may include any material that is substantially optically transparent including, but not limited to, glass and plastic. However, the desired substrate is a polymer film. Additionally, to aid in the binding on the substrate, the substrate desirably has a thin film of a metal or metal oxide coated on the film. However, if reflected light is used, non-optically transparent materials may be used.

Any film upon which a metal coating can be deposited is suitable for the present invention. These include, but are not limited to polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80%. Other suitable plastics and suppliers may be found, for example, in reference works such as the Modern Plastics Encyclopedia (McGraw-Hill Publishing Co., New York 1923–1996).

In one embodiment of the invention, the film with the metal coating thereon has an optical transparency of between approximately 5% and 95%. A more desired optical transparency for the film with the metal coating thereon used in the present invention is between approximately 20% and 80%. In a desired embodiment of the present invention, the film has at least an approximately 80% optical transparency, and the thickness of the metal coating is such as to maintain an optical transparency greater than about 20%, so that diffraction images can be produced by either reflected or transmitted light. However, in other embodiments of the invention, the metal thickness may be between approximately 1 nm and 2000 nm.

Metals that may be used for deposition on the film include gold, silver, aluminum, chromium, copper, iron, zirconium, platinum and nickel, as well as oxides of these metals.

In addition to the substrate, the diffraction based sensing devices also include a receptor material thereon that is specific for the analyte or analytes of interest. This receptor material is generally placed in a pattern on the substrate such that when the analyte binds to the receptor material, a specific diffraction image is formed.

In one possible embodiment, the receptor material is attached to an attachment layer that is located on the substrate. In some cases, the receptor material may be passively adhered to the attachment layer. If desired, the free functional groups introduced onto the test surface by the attachment layer may be used for covalent attachment of receptor material to the test surface. Chemistries available for attachment of receptor materials are well known to those skilled in the art.

In another embodiment, patterned antibody-binding protein is used as an attachment layer. Patterned antibody-binding protein layers with bound antibodies cause patterned placement or binding of analytes thereon.

In one embodiment of the present invention, the attachment layer is a self-assembling monolayer. Self-assembled monolayers of organic compounds on inorganic or metal surfaces are one aspect of one embodiment of the present invention. Although there are many different systems of self-assembling monolayers based on different organic components and supports, desired systems are those of alkanethiolates, $HS(CH_2)_nR$, on gold films. Typically, a gold film, 1 to 2000 nm thick, is supported on a titanium-primed $Si/SiO_2$ wafer or glass sheet. The titanium serves as an adhesion promoter between gold and the support. The alkanethiols chemisorb on the gold surface from a solution in which the gold film is immersed, and form adsorbed alkanethiolates with loss of hydrogen. Adsorption can also occur from the vapor. A wide variety of functional groups (R) can be incorporated into the surface or interior of the monolayer.

Self-assembling monolayers can therefore be tailored to provide a wide variety of material properties: such as wettability and protection against corrosion by chemical etchants. Additionally, the functional groups can be reactive to permit covalent attachment of the receptor material to the self-assembling monolayer.

In another embodiment, the receptor material may be directly applied to the substrate. In one particular embodiment of this principal, the receptor material is an antibody. The receptor material is characterized by an ability to specifically bind an analyte or analytes of interest. The variety of materials that may be used as receptor material are limited only by the types of material which will combine selectively (with respect to any chosen sample) with a secondary partner. Subclasses of materials which can be included in the overall class of receptor materials includes toxins, antibodies, antigens, hormone receptors, parasites, cells, haptens, metabolites, allergens, nucleic acids, nuclear materials, autoantibodies, cellular debris, enzymes, tissue proteins, enzyme substrates, coenzymes, neuron transmitters, viruses, viral particles, microorganisms, proteins, polysaccharides, chelators, drugs, and any other member of a specific binding pair. This list only incorporates some of the many different materials that can be used as the receptor material to produce a thin film assay system. Whatever the selected analyte of interest is, the receptor material is designed to bind specifically with the analyte of interest.

The diffraction based sensing devices with patterned receptors produced thereby may be used in one of two ways, depending on the size of the analyte. For analytes which are capable of causing diffraction by themselves, such as microorganisms, the system is used by first exposing the diffraction based sensing device to a medium that contains the analyte of choice and then, after an appropriate incubation period, transmitting a light, such as a laser, through the film or reflecting it off of the film. If the analyte is present in the medium and is bound to the receptor layer, the light is diffracted in such a way as to produce a visible image.

Optionally, for very small analytes such as proteins, the system may utilize "diffraction enhancing elements" which are capable of binding to the target analyte, and are capable of producing a substantial change in the height and/or refractive index, thereby increasing the diffraction efficiency of the biosensor and permitting the detection of smaller analytes. In use, a target analyte attaches either to the diffraction enhancing element, which then attaches to the diffraction based sensing device, or directly to select areas of the polymer film upon which the receptor is printed, with the diffraction enhancing element then binding to the analyte. Then diffraction of transmitted and/or reflected light occurs via the physical dimensions and defined, precise placement of the analyte and/or diffraction enhancing element. A diffraction image is produced which can be easily seen with the eye or, optionally, with a sensing device.

Another option for use of this sensor involves the detection of analytes which are antibodies. The sensing device could comprise only the patterned antibody-binding proteins, and then would be exposed to the medium having diffraction enhancing particles which have an antibody specific to the antibody to be detected. The selection of the antibody on the particle is preferably made so that it does not bind non-specifically to the patterned antibody-binding protein, but instead binds only when the analyte antibody is also bound. In this way, the diffraction enhancing elements would cause a substantial change in the height and/or refractive index if the analyte antibody is present, thereby causing a diffraction image to form.

Diffraction enhancing element particles that can be used in the present invention include, but are not limited to, glass, cellulose, synthetic polymers or plastics, latex, polystyrene, polycarbonate, metallic particles (e.g., gold microparticles, gold nanoparticles, silver precipitating agent, or silver microparticles, bacterial or fungal cells and so forth. The particles are preferably substantially spherical in shape, but the structural and spatial configuration of the particle is not critical to the present invention. For instance, the particles could be slivers, ellipsoids, cubes, and so forth. Particle sizes range from a diameter of about 0.1 μm to about 100.0 μm, desirably between about 0.3 μm to about 1 μm. The composition of the element particle is not critical to the present invention. Preferably, the difference in refractive index between the medium and the enhancing element is above 0.1.

The diffraction-based sensing device may also include the use of a wicking agent that is used to remove unbound labeled microparticles, as well as any residual liquid from the sample. The wicking agent avoids the necessity of any additional rinsing. Additionally, a small hole may be punched out of the center of the wicking agent so that once the sample and excess particles are wicked away, the hole allows the user to immediately check for a diffraction image without removing the wicking material. Examples of wicking agents include nitrocellulose membranes, cellulose acetate membranes, PVDF membranes, polypropylene, and glass microfiber structures.

In addition, the pore size of the wicking membrane may be varied to control the rate and force of wicking. This can affect the accuracy of the diagnostic device, and can also be taken advantage of to create a one-step device. To achieve this, the one-step device includes a contact printed capture antibody on a substrate, such as the gold/MYLAR®, which then has labeled particles pre-dried onto its surface. Additionally, a slow-wicking membrane with a hole cut out is placed on top of the device to complete it. The user simply adds the sample to be tested, and then views for a diffraction-image once wicking has occurred. The use of small pore sizes and/or hydrophobic materials or coatings can delay wicking long enough to allow adequate incubation, such as that needed for antibody-antigen interactions to take place. Alternatively, wicking may be delayed by using an erodible reagent at the periphery of the wicking agent circle. The reagent would eventually dissolve or derivatize so that it would allow wicking after a specific time period A wide range of techniques can be used to apply the receptor material to the substrate. Test surfaces may be coated with the receptor material by application of solution in discrete arrays or patterns; spraying, ink jet, or other imprinting methods; or by contact printing. The technique selected should minimize the amount of receptor material required for coating a large number of test surfaces and maintain the stability/functionality of receptor material during application. The technique must also apply or adhere the receptor material to the substrate in a very uniform and reproducible fashion.

In one such embodiment, the receptor material is printed using microcontact printing. An elastomeric stamp is used to transfer receptor material "ink" to a surface by contact; if the stamp is patterned, a patterned receptor material layer forms. The stamp may be fabricated by casting polydimethylsiloxane (PDMS) on a master having the desired pattern. Masters are prepared using standard photolithographic techniques, etching methods, or constructed from existing materials having microscale surface features.

In another embodiment, the receptor material is printed onto the substrate, such as a gold/MYLAR® substrate, in a defined pattern, using an ink-jet printer. A resolution of 720 dpi provides an array capable of producing a diffraction image upon binding by a target analyte and labeled microparticles. However, other resolutions may be used as well. The ink-jet printer still provides adequately small feature sizes (40–100 micron diameter) to give a diffraction image.

The analytes that are contemplated as being detected using the present invention include, but are not limited to, bacteria; yeasts; fungi; viruses; rheumatoid factor; antibodies, including, but not limited to IgG, IgM, IgA and IgE antibodies; carcinoembryonic antigen; *streptococcus* Group A antigen; viral antigens; antigens associated with autoimmune disease; allergens; tumor antigens; *streptococcus* Group B antigen; HIV I or HIV II antigen; or host response (antibodies) to these and other viruses; antigens specific to RSV or host response (antibodies) to the virus; an antigen; enzyme; hormone; polysaccharide; protein; lipid; carbohydrate; drug or nucleic acid; *Salmonella* species; *Candida* species, including, but not limited to *Candida albicans* and *Candida tropicalis; Salmonella* species; *Neisseria meningitides* groups A, B, C, Y and W sub 135, *Streptococcus pneumoniae, E. coli* K1, *Haemophilus influenza* type B; an antigen derived from microorganisms; a hapten, a drug of abuse; a therapeutic drug; an environmental agent; and antigens specific to hepatitis.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Examples 1–3

In Examples 1–3, an algorithm and method were determined for providing a yes/no answer through direct measurement(s) of the intensity of the diffracted beams.

The experimental setup included the following: a laser beam as the light source, a diffraction-based sensing sample, a mask, a photodiode, and several lenses. When the sample fulfilled the necessary conditions for diffraction (e.g., analyte was present), the orders of diffracted light beams were transmitted through the mask in its 0° (unrotated) position and the intensity was measured using the photodiode. Then the mask was rotated to block the diffracted beams by the mask, so they did not get registered by the photodiode; in this way, diffused or scattered light was measured. Measuring the intensity of the light in both positions of the mask allowed the portion of the diffused light and scattered beams to be excluded by accounting for these values.

Various algorithms were evaluated for accuracy with hundreds of samples. The orders of diffraction were each measured, starting with the $1^{st}$ order—the closest to the main, non-diffracted beam (zero order beam), and up—$2^{nd}$ order, $3^{rd}$ order, etc. Since some control samples showed the 1st diffraction order, this was taken into account by putting more weight on the intensity of the diffracted light from 2nd and upper orders. Based on data gathered from hundreds of samples studied, a specific loss of intensity with the rotation of the mask was selected for the cutoff level for an accurate yes/no decision. An artificial correction could be made to give a neutral zone between the positive and the negative results. A generic formula would include the ratio of M to R, wherein M is the intensity of diffracted light and R is the intensity of non-diffracted light; thus, the generic formulas of $X=(M-R)$ or $X=(M-R)/M$ could be used, where a value for 'X' above a certain threshold level would indicate a positive, analyte-containing sample that diffracts light.

A more specific example would have M represent the intensity of diffracted light intensity of the $2^{nd}$ and upper orders of diffracted light at 0° position of the mask, and R is the intensity of the non-diffracted light. This non-diffracted light could be measured through rotation of the same mask used to collect the $2^{nd}$ and upper orders, such that diffracted light is blocked by the mask and only diffused light is measured through the rotated mask. Again, the formula could be X'=(M−R) or X'=(M−R)/M. Also, loss of intensity (X) of the overall light source due to rotation of the mask could be measured.

In one embodiment, wherein 30% loss of intensity was used, the following formula was used:

If X>30%−$(M-R)^{1.6}$—the result is "positive",

If X≦30%−$(M-R)^{1.6}$—the result is "negative"

In another embodiment, the following formula was used:

IF $((M-R)>0.027-(M-R)^{1.6})$—the result is "positive"

IF $((M-R)<0.027-(M-R)^{1.6})$—the result is "negative"

Other embodiments used constantly-refining algorithms, which included factors based on the standard deviation of intensity reading averages. One example is:

IF $((M-R)>0.014-((-1)(0.12-X)^{1.7}))$ for X≦0.12— the result is "positive"

IF $((M-R)>0.014-X^3)$ for X>0.12—the result is "positive"

If the above criteria for (M−R) are not met, the result is "negative"

Example 4

As shown in FIG. 3, a hand-held analyzer was prepared with the following components: a laser diode as the light source; a means to hold a diffraction-based sensing sample such that light is transmitted through it; a mask that blocked all light except for the $1^{st}$, $2^{nd}$, $3^{rd}$, and $4^{th}$ diffraction orders; a photodiode; lenses and/or mirrors to direct the light; a microprocessor with memory capability; set of lights to indicate results; and LCD. All of these components were contained within a small, hand-held housing.

As soon as the analyzer is turned on, the LCD prompts the user for the necessary steps, such as "Insert Sample" then "Hit Test Button". If a diffracting sample was inserted into the sample holder, then the diffracted light intensity was collected by the photodiode, and a microprocessor converted the result as a "positive".

The microprocessor was programmed with the following algorithm:

A=Channel 1 reading/Channel 2 reading wherein channel 1 measured the intensity of the 2nd and upper order of diffracted light, while channel 2 measured the intensity of $1^{st}$ order diffracted light.

In one embodiment, wherein a cutoff of 2.0 was set, the following formula was used:

If X>2.0—the result is "positive",

If X<or equal to 2.0—the result is "negative"

In one set of samples, this cutoff value of 2.0 was found to provide accurate results for samples spiked with 1 μg/mL IgE (reading="positive"), and controls with 0 μg/mL IgE (reading="negative"). A positive reading was indicated by a red light that came on, as well as the message "Sample Positive" on the LCD. A negative reading was indicated by a green light that came on, as well as the message "Sample Negative" on the LCD. Readings could be obtained within about 5 seconds of placing the sample in the holder.

Of course, the microprocessor of the analyzer could also be programmed to register diffracting samples as "negative", if the opposite type of biosensor were configured.

The analyzers, methods and systems of the present invention can be used as a single test for detecting an analyte or it can be formatted as a multiple test device. They may be used to detect contamination in absorbent products, such as diapers, and to detect contamination by microorganisms.

In the present invention, the diffraction based sensing device can be attached to an adhesively backed sticker or decal which can then be placed on a hard surface or container wall. The diffraction based sensing device can be placed on the inside surface of a container such as a food package or a glass vial. The diffraction based sensing device can then be analyzed to determine the presence of an analyte.

As can be seen, the present invention provides an improved system and method of detecting an analyte by increasing the accuracy of the system by permitting the user to more easily view a diffraction image using a viewer, or by analyzing the diffraction image generated and providing a positive or negative reading, depending on whether the analyte is present in the sample.

We claim:

1. A method for detecting an analyte in a sample comprising:
   providing a substrate that contains a patterned receptor layer, the receptor layer containing a receptor material;
   binding the analyte to the patterned receptor layer on the substrate;
   contacting the analyte-bound substrate with incident light to thereby produce diffracted light;
   detecting the intensity of the diffracted light and the intensity of non-diffracted light; and
   performing an algorithm that contains as variables the intensity of the diffracted light and the intensity of the non-diffracted light, wherein the algorithm is defined by a formula: (the intensity of diffracted light at ≧1st orders)/(the intensity of the incident light) and the result of the algorithm is used to determine the presence of the analyte.

2. The method of claim 1, further comprising viewing the diffracted light.

3. The method of claim 1, wherein the incident light is in the visible spectrum.

4. The method of claim 1, wherein a light source containing an LED or a laser provides the incident light.

5. The method of claim 1, wherein the detection is accomplished with a detector that contains a photodiode.

6. The method of claim 1, wherein the intensity of the non-diffracted light is determined by measuring the intensity of the incident light before contacting the analyte-bound substrate.

7. The method of claim 1, wherein the intensity of the diffracted light used in the algorithm is determined primarily from upper order diffracted light.

8. The method of claim 1, wherein the intensity of the diffracted light is detected by blocking the non-diffracted light from a detector and then detecting the intensity of the diffracted light.

9. The method of claim 8, wherein the intensity of the diffracted light is detected by blocking the diffracted light from the detector and then detecting the intensity of the non-diffracted light.

10. The method of claim 9, wherein a mask is used to block the diffracted light and the non-diffracted light from the detector.

11. The method of claim 10, wherein the mask has a first orientation and a second orientation, wherein the diffracted light passes through the mask in the first orientation and the non-diffracted light passes through the mask in the second orientation.

12. The method of claim 11, wherein the intensity of the diffracted light is determined when the mask is in the first orientation.

13. The method of claim 12, wherein the intensity of the non-diffracted light is determined when the mask is in the second orientation.

14. The method of claim 1, further comprising informing a user of the presence or absence of the analyte.

15. The method of claim 1, wherein the patterned receptor layer is applied to a polymer film.

16. The method of claim 15, wherein a metal coating is present on the polymer film.

17. The method of claim 1, wherein the substrate has an optical transparency of between about 20% to about 80%.

18. The method of claim 1, wherein the incident light transmits light through the substrate.

19. The method of claim 1, wherein the incident light reflects from the substrate.

20. The method of claim 1, wherein the non-diffracted light includes zero-order light.

21. The method of claim 1, wherein the algorithm calculates the difference between the intensity of the diffracted light and the intensity of the non-diffracted light.

22. A method for detecting an analyte in a sample comprising:

providing a substrate that contains a patterned receptor layer applied to a polymer film, the receptor layer containing a receptor material;

binding the analyte to the patterned receptor layer;

contacting the analyte-bound substrate with incident light to thereby produce diffracted light;

positioning a mask in a first orientation to block non-diffracted light from a detector and then detecting the intensity of the diffracted light;

positioning a mask in a second orientation to block the diffracted light from the detector and then detecting the intensity of the non-diffracted light; and performing an algorithm that contains as variables the intensity of the diffracted light and the intensity of the non-diffracted light, wherein the algorithm is defined by a formula: (intensity of the diffracted light at $\geq$1st orders)/(intensity of the incident light), and the result of the algorithm is used to determine the presence of the analyte.

23. The method of claim 22, wherein the algorithm calculates the difference between the intensity of the diffracted light and the intensity of the non-diffracted light.

* * * * *